(12) United States Patent
Bian et al.

(10) Patent No.: US 11,064,880 B2
(45) Date of Patent: Jul. 20, 2021

(54) EYE REFRACTIVE POWER MEASURING DEVICE AND METHOD OF MEASURING EYE REFRACTIVE POWER

(71) Applicant: TOMEY CORPORATION, Nagoya (JP)

(72) Inventors: Guangchun Bian, Ichinomiya (JP); Daisuke Santo, Nagoya (JP)

(73) Assignee: Tomey Corporation, Nagoya (JP)

( * ) Notice: Subject to any disclaimer, the term of this patent is extended or adjusted under 35 U.S.C. 154(b) by 74 days.

(21) Appl. No.: 16/420,584

(22) Filed: May 23, 2019

(65) Prior Publication Data
US 2019/0365221 A1  Dec. 5, 2019

(30) Foreign Application Priority Data

May 31, 2018 (JP) .............................. JP2018-104694

(51) Int. Cl.
*A61B 3/103* (2006.01)
*A61B 3/12* (2006.01)
*A61B 3/00* (2006.01)

(52) U.S. Cl.
CPC ............ *A61B 3/103* (2013.01); *A61B 3/0008* (2013.01); *A61B 3/0033* (2013.01); *A61B 3/0041* (2013.01); *A61B 3/12* (2013.01)

(58) Field of Classification Search
CPC ....... A61B 3/0008; A61B 3/0033; A61B 3/12; A61B 3/14; A61B 3/00; A61B 3/0041; A61B 3/0075; A61B 3/032; A61B 3/036; A61B 3/09; A61B 3/103; A61B 3/1173; A61B 3/152; A61B 3/028

USPC ........ 351/200, 205–206, 209–211, 221–223, 351/243–246
See application file for complete search history.

(56) References Cited

U.S. PATENT DOCUMENTS

| 5,940,165 A | 8/1999 | Isogai et al. |
| 2007/0070293 A1* | 3/2007 | Isogai .................... A61B 3/103 351/205 |
| 2011/0128498 A1 | 6/2011 | Nakamura |

FOREIGN PATENT DOCUMENTS

| EP | 1138252 | 10/2001 |
| JP | H1043136 | 2/1998 |
| JP | H1094516 | 4/1998 |

(Continued)

OTHER PUBLICATIONS

Extended Search Report from European Appln. No. 19176377.0, dated Nov. 4, 2019.

*Primary Examiner* — Brandi N Thomas
(74) *Attorney, Agent, or Firm* — Grossman, Tucker, Perreault & Pfleger, PLLC

(57) ABSTRACT

A measuring device according to one aspect of the present disclosure projects a measuring light toward a fundus of a subject's eye; receives a reflected light reflected from the fundus; and then measures an eye refractive power of the subject's eye based on a light-receiving signal. Additionally, reliability of a measured value is determined. Specifically, a process, in which the eye refractive power is measured based on the light-receiving signal, is consecutively executed an undetermined number of times until an end condition is satisfied. The measured value of the eye refractive power obtained in every execution of the process is displayed on a display together with information indicating the reliability of the measured value.

20 Claims, 10 Drawing Sheets

(56) References Cited

FOREIGN PATENT DOCUMENTS

| | | |
|---|---|---|
| JP | H10216088 | 8/1998 |
| JP | 2014150857 | 8/2014 |

\* cited by examiner

EYE REFRACTIVE POWER MEASURING DEVICE AND METHOD OF MEASURING EYE REFRACTIVE POWER

CROSS-REFERENCE TO RELATED APPLICATIONS

The present application claims the benefit of Japanese Patent Application No. 2018-104694 filed on May 31, 2018 with the Japan Patent Office, the entire disclosure of which is incorporated herein by reference.

BACKGROUND

The present disclosure relates to an eye refractive power measuring device and a method of measuring the eye refractive power.

A measuring device for measuring an eye refractive power has been already known. In order to obtain an accurate measured value, measurement is preferably executed with a subject's eye being positioned properly with respect to a measurement system and the subject's eye being relaxed. To achieve this, a conventional measuring device includes a function to detect alignment state of a subject's eye and a function to place a target out of focus (fogging state). For example, the measuring device measures an eye refractive power if the alignment state is properly established. The measuring device executes preliminary measurement in advance of a main measurement of the eye refractive power. The measuring device then places the target into the fogging state based on a result of the preliminary measurement, to thereby relax the subject's eye.

As disclosed in Japanese Unexamined Patent Application Publication No. H10-94516, also known is a measuring device that consecutively measures an eye refractive power multiple time. This measuring device calculates reliability of measured values and selectively displays a measured value having higher reliability on a display based on information on calculated reliability. Alternatively, this measuring device weights each measured value obtained in each measurement based on the information on the reliability and displays a weighted average of the measured values on the display.

SUMMARY

Measurement of the eye refractive power is targeted not only to an adult but also to a child. With respect to eyes of a child, it is difficult to execute proper measurement due to restlessness of the child. For example, in order to place the target into the fogging state, it is necessary to execute preliminary measurement of a refractive power on a subject's eye. However, the preliminary measurement takes time to start if remaining unexecuted until the alignment state is properly established so that the fogging state is properly created.

If the subject is a child, the alignment state changes drastically. Even if the preliminary measurement is executed after the alignment state is properly established, the alignment state during the preliminary measurement is not proper in many cases due to the drastic change in the alignment state.

Even if consecutive measurement is executed a specific number of times, a measurement value of each measurement or a measured value of nearly every measurement has lower reliability. As a result, it may be necessary to execute the consecutive measurement again. There exists a tendency that the longer the measurement takes, the more a child becomes uncooperative for the measurement. This tendency makes it difficult to properly execute the measurement on a child.

In one aspect of the present disclosure, it is desired to provide an eye refractive power measuring device and a method of measuring the eye refractive power are advantageously suitable for a restless subject including a child.

An eye refractive power measuring device of one aspect of the present disclosure comprises a light projector, a light receiver, and a controller. The controller is configured to project a measuring light toward a fundus of a subject's eye. The light receiver is configured to receive a reflected light that is reflected from the fundus.

The controller is configured to execute a process that measures an eye refractive power of the subject's eye an undetermined number of times based on a light-receiving signal from the light receiver until an end condition is satisfied. The controller is further configured to determine reliability of a measured value of the eye refractive power in every execution of the process. The controller is further configured to display, in every execution of the process, the measured value on a display together with information indicating the reliability.

Disclosers of the present disclosure has found that sporadic measurement that is executed after the alignment state is properly established has no significant contribution to the restless subject in terms of enhancement of measurement accuracy. In comparison with the sporadic measurement, consecutive measurement of the eye refractive power can increase the number of measurement per unit time. This consequently increases a possibility in which a measured value having enhanced reliability is obtained as much as possible within a short period of time.

According to the present disclosure, it is also significant in that an examiner can properly grasp a situation, based on information displayed on the display, on whether proper measurement is executed. This grasp enables the examiner to properly deal with the situation and to end the proper measurement within the short period of time. Thus, in one aspect of the present disclosure, it is possible to provide an eye refractive power measuring device that is adapted advantageously for the restless subject.

According to another aspect of the present disclosure, the controller may be configured to start consecutive execution of the process without executing automatic fogging. The automatic fogging may be a process to place a target, which is presented to the subject's eye, into a fogging state. The automatic fogging may be a process to place the target into the fogging state based on a preliminarily measured value of the eye refractive power of the subject's eye. The automatic fogging may be a process to place the target into the fogging state by changing a distance between the subject's eye and the target.

The automatic fogging has a poor effect on the restless subject. In general, executing proper automatic fogging requires waiting until the alignment state is properly established and thereafter executing the preliminary measurement of the eye refractive power. In this case, it takes time to start a main measurement. If consecutive execution of the process starts without the automatic fogging, then it is possible to promptly execute the consecutive measurement of the eye refractive power.

According to another aspect of the present disclosure, the measuring device may comprise an inputter that is configured to input a command from an operator. The controller may be configured to start the consecutive execution of the process on a condition that a start command is input through the inputter. Satisfaction of the end command may be that an end command is input through the inputter. The controller may be configured to consecutively execute the process during a time interval from input of a start command through the inputter to input of the end command.

An end of the consecutive measurement in accordance with the end command allows the measuring device to continue the consecutive measurement until a required measurement result is obtained and enables an operation that ends the measurement promptly in response to obtainment of the required measurement result.

According to another aspect of the present disclosure, the controller may be configured to display the measured value on the display in a display mode that corresponds to the reliability among specific display modes. The controller may be configured to display the measured value on the display in a color that corresponds to the reliability among specific colors. Colored display of the reliability enables the examiner to easily grasp an examination status.

According to another aspect of the present disclosure, the controller may be configured to display, in a list display area of the display, a list of measured values of the eye refractive power obtained through execution of the process multiple times. Listing and displaying of the measured values enables the examiner to deeply grasp a status of an eye examination through the consecutive measurement.

According to another aspect of the disclosure, the controller may be configured, in every execution of the process, to add a measured value of the eye refractive power obtained through a corresponding measurement process in the list display area.

The controller may be configured to delete, from the list display area, a measured value that has the lowest reliability among the measured values of the eye refractive power already displayed in the list display area when the list display area lacks an area to display a newly measured value of the eye refractive power in the list display area.

According to another aspect of the present disclosure, the controller may be configured to display, in a temporal display area in the display, the latest measured value among measured values of the eye refractive power obtained through execution of the process multiple times. The controller may be further configured to display, in a list display area in the display, a list of measured values having reliability equal to or greater than standard reliability among the measured values of the eye refractive power obtained thorough the execution of the process multiple times.

According to another aspect of the present disclosure, the controller may be configured to arrange the measured values displayed in the list display area in an order that corresponds to individual reliability. With this configuration, it is possible to provide the examiner with the examiner's desired information in an easily understandable manner.

According to another aspect of the present disclosure, the eye refractive power measuring device may comprise a detector that is configured to detect a position of the subject's eye. The reliability of the measured value varies depending on an amount of positional deviation of the subject's eye with respect to the measurement system. Accordingly, the controller may be configured to determine the reliability of the measured value based on the position of the subject's eye that is detected by the detector.

The controller may be further configured to determine the reliability based on spatial distribution of the reflected light that is indicated by the light-receiving signal. The reliability of the measured value can be evaluated in accordance with the spatial distribution of the reflected light, specifically, image quality of a received light in one example. Thus, with the above configuration, it is possible to more properly determine the reliability.

According to another aspect of the present disclosure, the controller may be configured to measure the eye refractive power in either one of operation modes. The operation modes may include a first operation mode and a second operation mode. The controller placed in the first operation mode may execute automatic fogging and thereafter measure the eye refractive power based on the light-receiving signal from the light receiver. The controller placed in the second operation mode may start consecutive execution of the process without executing the automatic fogging.

According to another aspect of the present disclosure, the controller may be configured, in response to a specific condition being satisfied after the controller starts operating in the first operation mode, to start operating in the second operation mode in place of the first operation mode, to thereby start the consecutive execution of the process without executing the automatic fogging. The controller may be configured to start operating in the second operation mode on a condition that measurement of the eye refractive power of in the first operation mode is failed. The controller may be configured to start operating in the second operation mode on a condition that the reliability of the measured value of the eye refractive power in the first operation mode is below specific standard reliability.

According to another aspect of the present disclosure, provided may be a computer-implemented method of measuring an eye refractive power. The method of measuring the eye refractive power may comprise: consecutively executing a process an undetermined number of times until an end condition is satisfied, the process including projecting a measuring light toward a fundus of a subject's eye, obtaining a light-receiving signal from the optical system that is configured to receive a reflected light reflected from the fundus, and measuring an eye refractive power of the subject's eye based on the light-receiving signal; determining reliability of a measured value of the eye refractive power in every execution of the process; and displaying, in every execution of the process, the measured value on a display together with information that indicates the reliability.

In another aspect of the present disclosure, provided may be a computer program that causes a computer to execute a method of measuring the eye refractive power and/or a recording medium that records the computer program.

BRIEF DESCRIPTION OF THE DRAWINGS

An embodiment of the present disclosure will be described hereinafter by way of example with reference to the accompanying drawings, in which.

DETAILED DESCRIPTIONS OF THE EMBODIMENT

Figure 1:
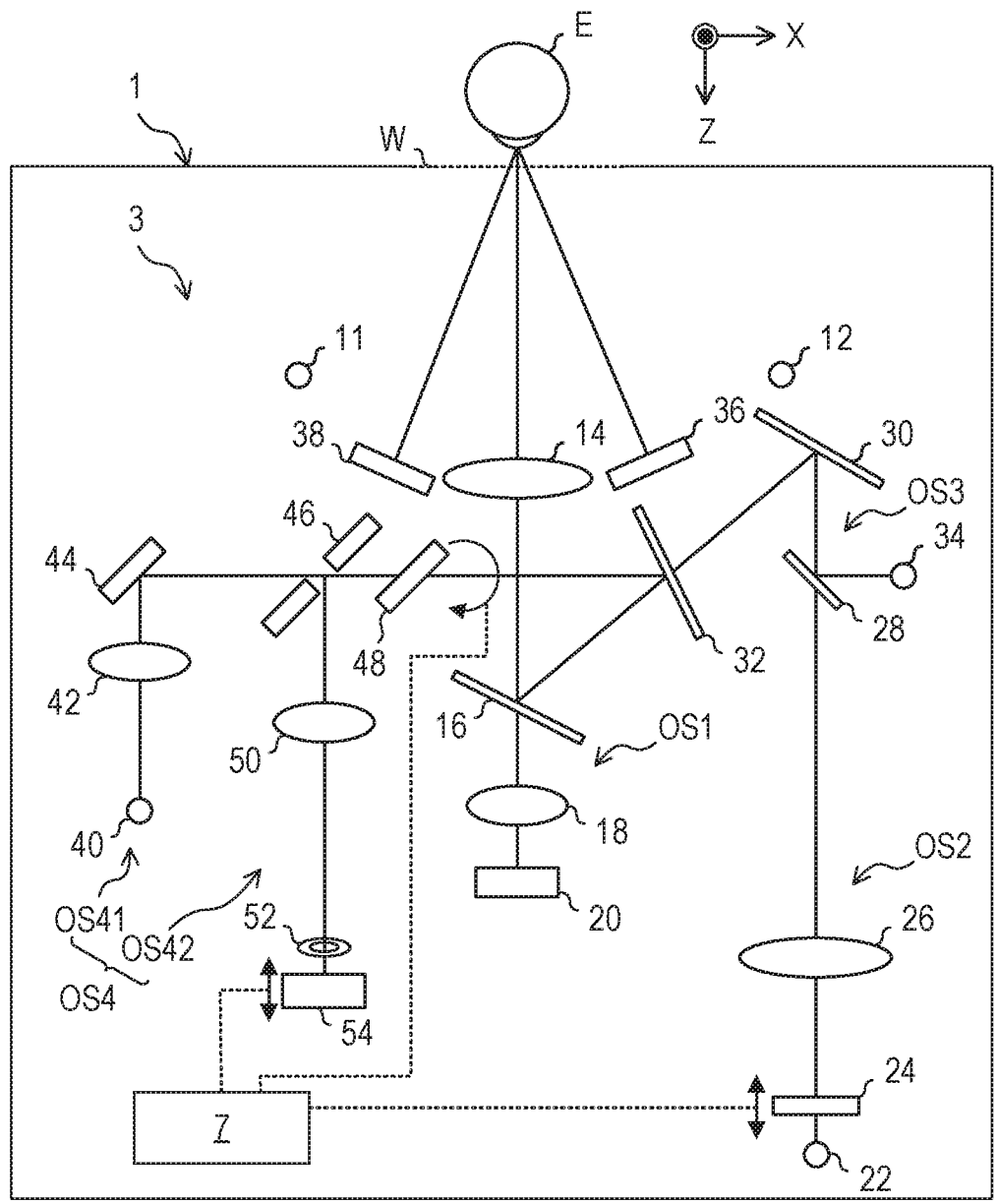
FIG. 1 is a view of a schematic configuration showing an optical system of a measuring device.

A measuring device 1 of the present embodiment shown in FIG. 1 is an eye refractive power measuring device. The measuring device 1 projects a measuring light onto a fundus of a subject's eye E through a window W. The measuring device 1 receives a reflected light that is reflected from the fundus and corresponds to the measuring light. Based on a light-receiving signal, the measuring device 1 measures a refractive power of the subject's eye E (hereinafter, appropriately referred to as eye refractive power).

As shown in FIG. 1, the measuring device 1 comprises a device optical system 3 and a control system 7. The device optical system 3 comprises an observation optical system OS1, a target optical system OS2, an alignment detection optical system OS3, and an eye refractive power measuring optical system OS4.

The observation optical system OS1 is placed to observe an anterior segment of the subject's eye E. The target optical system 052 is placed to present a target 24. The alignment detection optical system 053 is placed to detect a position of the subject's eye E with respect to the device optical system 3. The eye refractive power measuring optical system 054 is placed to measure the refractive power of the subject's eye E.

The observation optical system 051 is configured mainly with illumination light sources 11 and 12, a lens 14, a hot mirror 16, a lens 18, and an imaging element for observation 20. The illumination light sources 11 and 12 are configured to irradiate an infrared light, for example having a wavelength of 780 nm. The hot mirror 16 is configured to transmit the infrared light from the illumination light sources 11 and 12 therethrough. Additionally, the hot mirror 16 is configured to reflect respective lights from an alignment light source 34, a measuring light source 40, and a target light source 22.

In the observation optical system OS1, the infrared light that are irradiated from the illumination light sources 11 and 12 and reflected on the anterior segment of the subject's eye E penetrate through the hot mirror 16 through the lens 14 and are led onto the imaging element for observation 20 through the lens 18.

The target optical system 052 is configured mainly with the target light source 22, the target 24, a lens 26, a semitransparent mirror 28, a reflective mirror 30, a hot mirror 32, the hot mirror 16, and the lens 14. As can be understood from this description, the target optical system 052 includes some optical members that are commonly used in the observation optical system OS1.

The target light source 22 is configured to irradiate a visible light, for example having a wavelength of 400 nm to 700 nm. The target 24 is positioned to be movable in optical-axis directions. Movement of the target 24 is controlled by the control system 7.

The semitransparent mirror 28 is configured to transmit the light from the target light source 22 therethrough and reflect the light from the alignment light source 34. The hot mirror 32 is configured to transmit the respective lights from the target light source 22 and the alignment light source 34 therethrough and to reflect the light from the measuring light source 40.

In the target optical system OS2, the light emitted from the target light source 22 penetrates through the lens 26 and the semitransparent mirror 28 through the target 24 and is thereafter reflected on the reflective mirror 30. The light reflected on the reflective mirror 30 further penetrates through the hot mirror 32 and is reflected on the hot mirror 16, and is then irradiated on the subject's eye E through the lens 14.

The alignment detection optical system OS3 is configured mainly with the alignment light source 34, the semitransparent mirror 28, the reflective mirror 30, the hot mirror 32, the hot mirror 16, the lens 14, and alignment detection sensors 36 and 38 (in other words, profile sensors).

The alignment light source 34 is configured to irradiate an infrared light having a wavelength of 810 nm, for example. The light from the alignment light source 34 is reflected on the semitransparent mirror 28 and is then reflected on the reflective mirror 30. The reflected light penetrates through the hot mirror 32 and is reflected on the hot mirror 16, and is then irradiated on the subject's eye E through the lens 14. This irradiated light is reflected on a cornea of the subject's eye E and is led onto the alignment detection sensors 36 and 38.

The eye refractive power measuring optical system OS4 includes a light-projecting optical system OS41 and a light-receiving optical system OS42. The light-projecting optical system OS41 is configured mainly with the measuring light source 40, a lens 42, a reflective mirror 44, a perforated mirror 46, a parallel planar plate 48, the hot mirror 32, the hot mirror 16, and the lens 14.

The light-receiving optical system OS42 is configured mainly with a lens 50, a ring lens 52, and an imaging element for measurement 54, and optical members that are commonly used in the light-projecting optical system OS41. The commonly used optical members are the lens 14, the hot mirror 16, the hot mirror 32, the parallel planar plate 48, and the perforated mirror 46.

The measuring light source 40 is configured with a super luminescent diode (SLD) having an enhanced coherence, for example. The measuring light source 40 is configured to emit an infrared light, for example having a wavelength of 880 nm, as a measuring light beam. The imaging element for measurement 54 is configured to be movable in the optical-axis directions. Movement of the imaging element for measurement 54 is controlled by the control system 7.

The parallel planar plate 48 is positioned in an optical path shared between the light-projecting optical system OS41 and the light-receiving optical system OS42. Specifically, the parallel planar plate 48 is positioned to rotate about an optical axis of the shared optical path while inclining with respect to the optical axis so that the measuring light beam enters in a position spaced a specific distance from the center of a pupil of the subject's eye E. The rotation of the parallel planar plate 48 is controlled by the control system 7. The rotation of the parallel planar plate 48 causes the measuring light beam to rotate circumferentially on the pupil of the subject's eye E. This rotation can inhibit a speckle noise generated due to use of a light source having an enhanced coherence. The parallel planar plate 48 is placed at a position conjugate with the pupil of the subject's eye, for example.

The measuring light beam from the measuring light source 40 is reflected on the reflective mirror 44 through the lens 42, passes through a hole located in the center of the perforated mirror 46 and through the parallel planar plate 48, and is then reflected on the hot mirror 32 and the hot mirror 16. The light beam reflected on the hot mirror 16 is irradiated on the fundus of the subject's eye through the lens 14. The light beam reflected on the fundus of the subject's eye E is reflected on the hot mirror 16 and the hot mirror 32 through the lens 14 and then passes through the parallel planar plate 48. The light beam passed through the parallel planar plate 48 is reflected on a ring-shaped mirror portion in the perforated mirror 46 and is thereafter led onto the imaging element for measurement 54 through the lens 50 and the ring lens 52.

The device optical system 3 having the above-descried configuration is positioned such that the entirety of the device optical system 3 is displaceable along an X-axis, a Y-axis, and a Z-axis. Displacement of the device optical system 3 is controlled by the control system 7. The displacement is executed for positioning between the subject's eye E and the device optical system 3. Here, the X-axis corresponds to left-right directions, the Y-axis corresponds to up-down directions, and the Z-axis corresponds to front-rear directions, which correspond to the optical axis directions.

Figure 2:
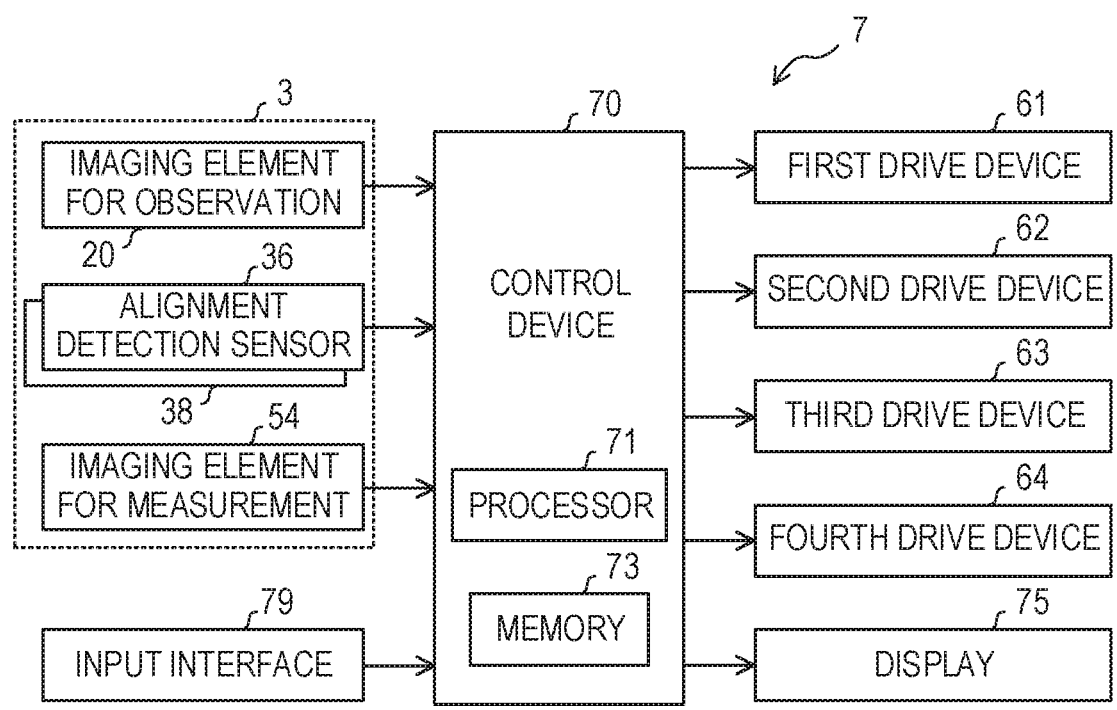
FIG. 2 is a block diagram showing a control system of the measuring device.

As shown in FIG. 2, the control system 7 comprises a first drive device 61, a second drive device 62, a third drive device 63, a fourth drive device 64, a control device 70, a display 75, and an input interface 79.

The first drive device 61 is configured to be controlled by the control device 70 to move the target 24 in the optical-axis directions. The second drive device 62 is configured to be controlled by the control device 70 to rotate the parallel planar plate 48 about the optical axis. The third drive device 63 is configured to be controlled by the control device 70 to move the imaging element for measurement 54 in the optical-axis directions. The fourth drive device 64 is configured to be controlled by the control device 70 to move the device optical system 3 along the X-axis, the Y-axis, and the Z-axis.

The control device 70 is coupled to the first drive device 61, the second drive device 62, the third drive device 63, the fourth drive device 64, the display 75, the input interface 79, the imaging element for observation 20, the alignment detection sensors 36 and 38, and the imaging element for measurement 54.

The control device 70 comprises a processor 71 and a memory 73. The memory 73 includes a ROM, a RAM, and a flash memory. The processor 71 controls the measuring device 1 in accordance with a computer program stored in the memory 73 to execute processes for achieving various functions.

The display 75 comprises a liquid crystal display (LCD), for example. The display 75 is controlled by the control device 70 to display various information for an examiner. The input interface 79 comprises a lever and a key switch to allow the examiner to operate the measuring device 1. The input interface 79 functions as an inputter or an operator. The input interface 79 inputs a command signal from the examiner to the control device 70.

The control system 7 may further comprise a not-shown printing device to provide the examiner with a measurement result in the form of a printed material. The control system 7 may comprise a data communication device to provide an external information processing device with the measurement result.

The control device 70 obtains an image signal from the imaging element for observation 20, the image signal indicating a photographic image of the anterior segment. Based on this image signal, the control device 70 displays the photographic image of the anterior segment on the display 75 (see, FIG. 7).

Further, the control device 70 obtains respective detection signals from the alignment detection sensors 36 and 38. The detection signals indicate received light distribution of corneal reflected light (spotted light) that is received in the alignment detection sensors 36 and 38.

Based on the respective detection signals from the alignment detection sensors 36 and 38, the control device 70 calculates three dimensional positional coordinates (in other words, X-positional coordinate, Y-positional coordinate, and Z-positional coordinate) of the subject's eye E, as an alignment index value, with respect to the device optical system 3. The control device 70 controls the fourth drive device 64 based on the alignment index value if necessary. This allows the positioning between the device optical system 3 and the subject's eye E.

The control device 70 further obtains a light-receiving signal of a ring image from the imaging element for measurement 54, the ring image being imaged on the imaging element for measurement 54, in other words, corresponding to the measuring light beam reflected on the fundus of the subject's eye E. Based on this ring image indicated by the light-receiving signal, the control device 70 measures the refractive power of the subject's eye E.

Specifically, the control device 70 detects positional coordinates of the ring image. Based on the detected positional coordinates of the ring image, the control device 70 executes ellipse approximation of the ring image using least squares technique or the like. Based on a shape of the approximated ellipse, the control device 70 calculates a refractive value including S (spherical power), C (cylindrical power), and A (astigmatic axis angle) as a measured value associated with the refractive power of the subject's eye E. The control device 70 displays the calculated measured value of the subject's eye E on the display 75. The control device 70 stores this measured value in the memory 73 as a measurement history data.

The measurement history data is stored in the memory 73, particularly in the flash memory for the purpose of providing the examiner with the measurement result in accordance with a request from the examiner after an examination ends, for example. For example, the measurement history data is stored in order to be presented to the examiner as a printed material or to be transferred to the external information processing device.

Figure 3:
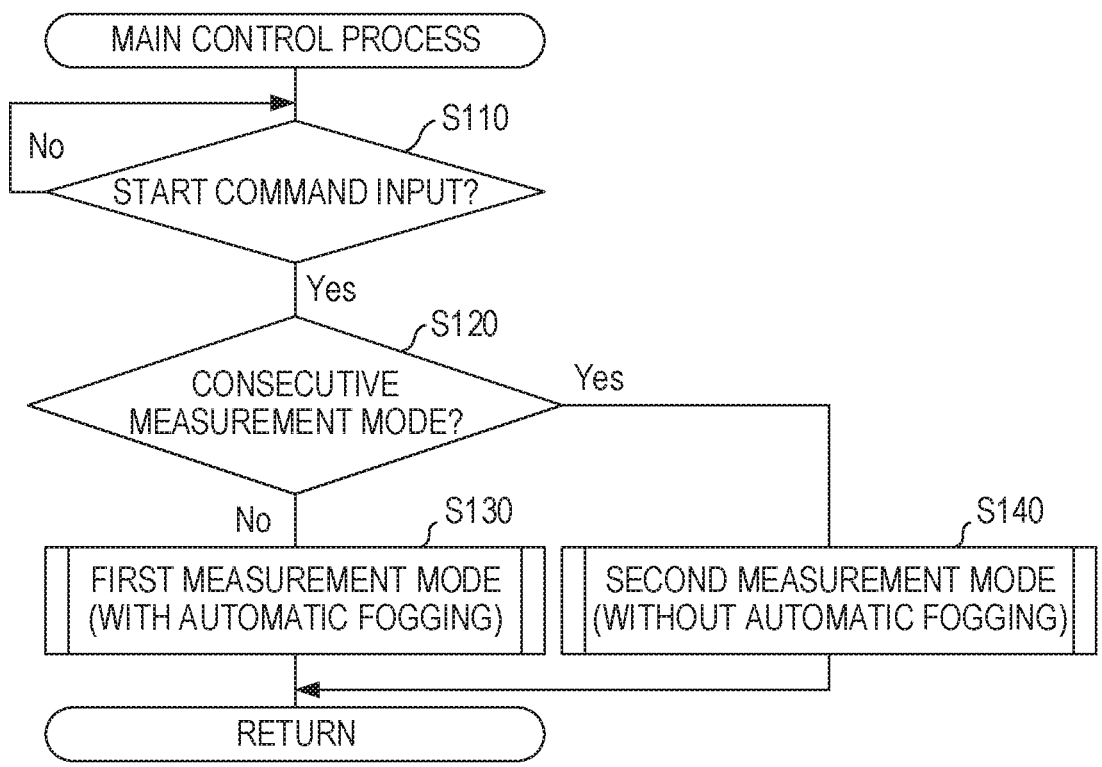
FIG. 3 is a flowchart showing a main control process executed by a control device.

A description is now given in detail to a process executed by the control device 70 for measurement of the eye refractive power. The control device 70 is configured to repeatedly execute a main control process shown in FIG. 3. In the main control process, the control device 70 waits until a start command is input from the examiner through the input interface 79 (S110). In response to input of the start command (S110: Yes), the control device 70 determines whether a measurement mode selected from measurement modes is a consecutive measurement mode (S120).

The control device 70 displays a graphical user interface for mode selection on the display 75, to thereby accept, through the input interface 79, operation made by the examiner for measurement mode selection.

In response to determination that the selected measurement mode is not the consecutive measurement mode (S120: No), the control device 70 executes a first measurement process that corresponds to a standard measurement mode (S130). In response to determination that the selected measurement mode is the consecutive measurement mode (S120: Yes), the control device 70 executes a second measurement process that corresponds to the consecutive measurement mode (S140). Then, the control device 70 ends the main control process.

In the first measurement process (S130), the control device 70 executes automatic fogging and thereafter measures the refractive power of the subject's eye E.

Figure 4:
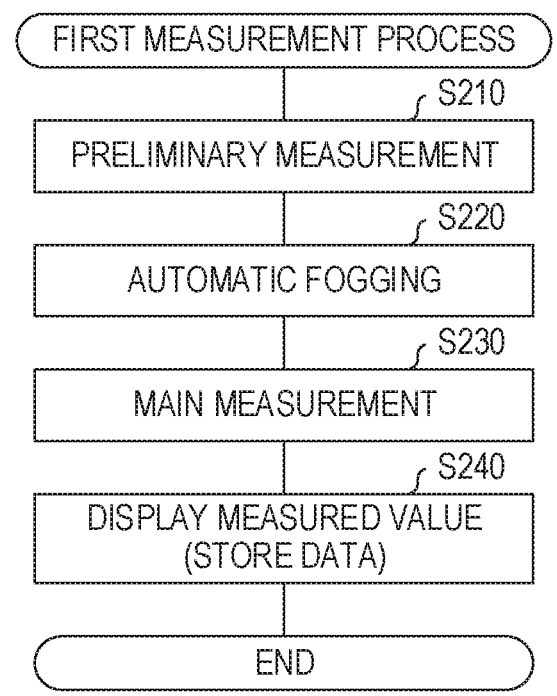
FIG. 4 is a flowchart showing a first measurement process executed by the control device.

As shown in FIG. 4, in response to a start of the first measurement process, the control device 70 executes preliminary measurement of the refractive power of the subject's eye E (S210). In the preliminary measurement, the refractive power of the subject's eye E is measured for the purpose of properly placing the target 24 into a fogging state. Specifically, the control device 70 controls the fourth drive device 64 based on the above-described alignment index value, to thereby adjust a position of the device optical system 3 along the X-axis, the Y-axis, and the Z-axis with respect to the subject's eye E. In other words, the control device 70 positions the device optical system 3 with respect to the subject's eye E.

Then, the control device 70 lights the measuring light source 40 to project a spotted image of a point light source on the fundus of the subject's eye E with the parallel planar plate 48 being rotated. The image of the point light source projected on the fundus is reflected and is then imaged into a ring-shape on the imaging element for measurement 54 though the ring lens 52. During this, the control device 70 moves the imaging element for measurement 54 in the optical axis directions to form the brightest and narrowest ring image on the imaging element for measurement 54. Based on this ring image, the control device 70 executes the preliminary measurement of the refractive power of the subject's eye E.

In response to end of the preliminary measurement (S210), the control device 70 executes the automatic fogging based on the measured value of the refractive power obtained in the preliminary measurement (S220). Specifically, the control device 70 moves the target 24 in the optical axis directions to thereby place the target 24 at a position conjugate with the fundus of the subject's eye E. Then, the control device 70 moves the target 24 by a distance that corresponds to an appropriate diopter to thereby place the target 24 in the fogging state with respect to the subject's eye E (S220).

The control device 70 executes a main measurement with the target 24 remaining in the fogging state (S230). Specifically, as in the preliminary measurement, the control device 70 lights the measuring light source 40 to form a ring image on the imaging element for measurement 54. The control device 70 measures the refractive power of the subject's eye E based on the light-receiving signal that is input from the imaging element for measurement 54.

Then, the control device 70 displays the measured value of the refractive power on the display 75 and stores this measured value in the memory 73 as the measurement history data (S240). Then, the control device 70 ends the first measurement process (S130).

Figure 5:
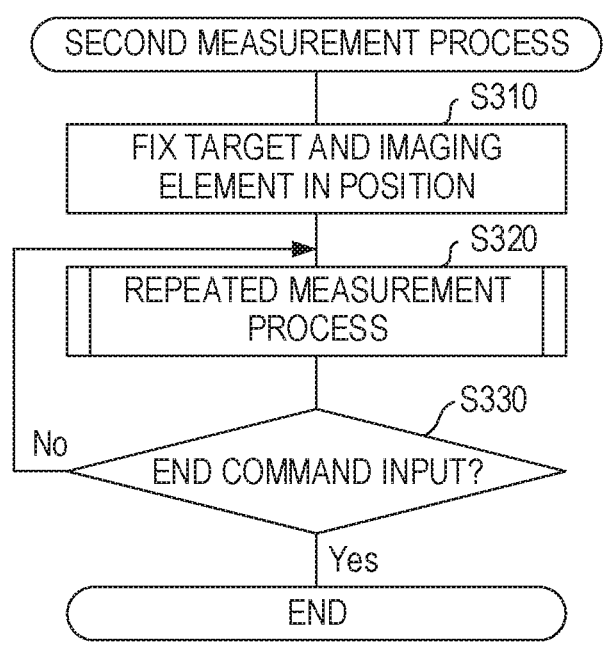
FIG. 5 is a flowchart showing a second measurement process executed by the control device.

In the second measurement process (S140) shown in FIG. 5, the control device 70 consecutively measures the refractive power of the subject's eye E without executing the preliminary measurement and the automatic fogging. In response to a start of the second measurement process, the control device 70 fixes the target 24 and the imaging element for measurement 54 in respective standard positions without measuring the refractive power of the subject's eye E in the preliminary measurement and without executing the automatic fogging based on the measured value measured in the preliminary measurement (S310). The respective standard positions are set in advance.

In another example, the control device 70 may fix the target 24 and the imaging element for measurement 54 in respective positions selected by the examiner through the input interface 79, instead in the respective standard positions. The control device 70 may control the fourth drive device 64 to place the device optical system 3 in a standard position or in a position selected by the examiner through the input interface 79.

Figure 6:
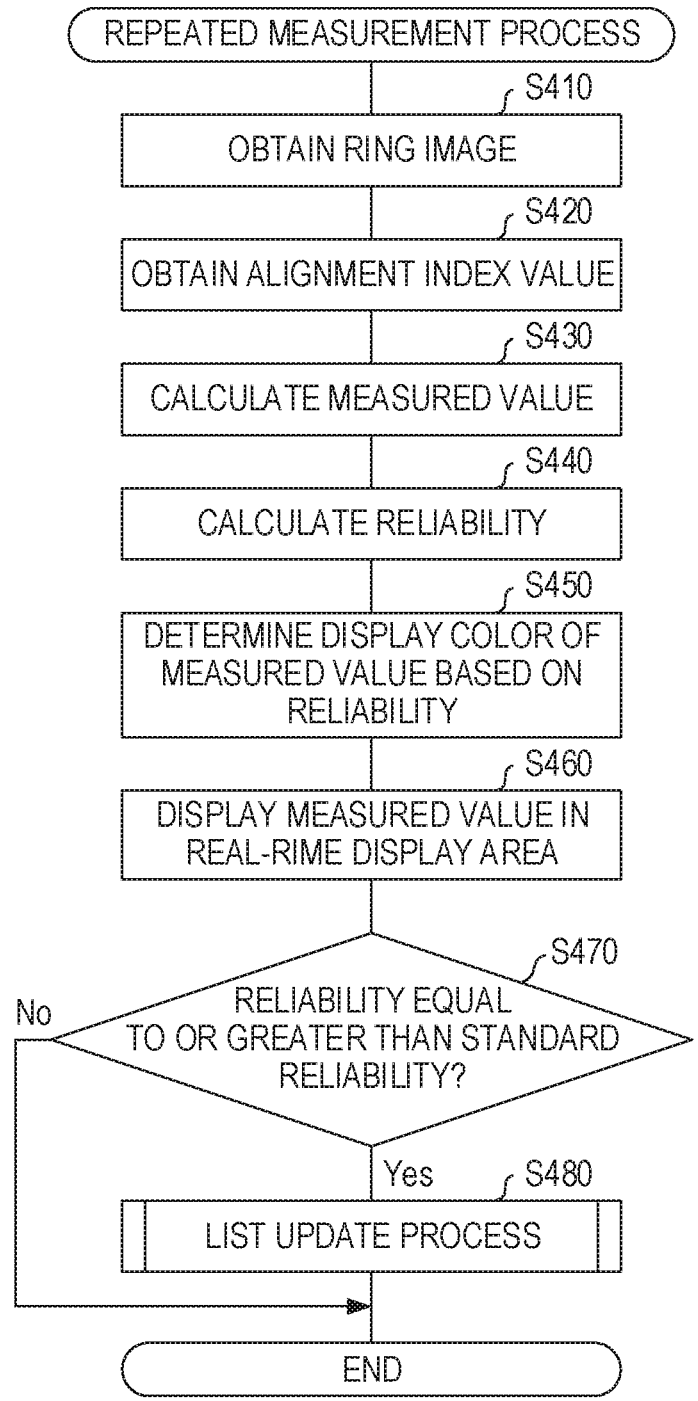
FIG. 6 is a flowchart showing a repeated measurement process executed by the control device.

Then, the control device 70 consecutively and repeatedly executes a repeated measurement process (S320) shown in FIG. 6 until an end command is input by the examiner through the input interface 79. In response to input of the end command (S330: Yes), the control device 70 ends the second measurement process, to thereby end the consecutive measurement of the refractive power.

In response to a start of the repeated measurement process, the control device 70 obtains a ring image (S410). Specifically, the control device 70 lights the measuring light source 40 to form the ring image on the imaging element for measurement 54. From the imaging element for measurement 54, the control device 70 obtains a light-receiving signal that indicates the ring image.

Further, the control device 70 obtains an alignment index value of the subject's eye E at the time when the ring image is formed (S420). In S420, the control device 70 obtains respective detection signals from the alignment detection sensors 36 and 38. Based on these detection signals, three dimensional positional coordinates of the subject's eye E with respect to the device optical system 3 are calculated as the alignment index value.

Then, the control device 70 calculates a measured value of the refractive power based on the ring image that is indicated by the light-receiving signal and obtained in S410 (S430). The measured value includes a refractive value including S (spherical power), C (cylindrical power), and A (astigmatic axis angle) that are associated with the subject's eye E.

Further, the control device 70 calculates reliability of the latest measured value calculated in S430 (S440). The calculated reliability may be any one of the following scores Z1, Z2, Z3, or Z4, or may be a weight sum of two or more of the scores Z1, Z2, Z3, or Z4.

The score Z1 is based on an alignment error between the subject's eye E and the device optical system 3. The alignment error can be deviation D (dX, dY, dZ) of three dimensional positional coordinates P (X, Y, Z) of the subject's eye E with respect to the device optical system 3 from the standard position P0 (X0, Y0, Z0), in other words, calculated as follows: (dX, dY, dZ)=P−P0. The score Z1 is defined to show a smaller value as the alignment error (absolute value) increases and to show a greater value as the alignment error decreases. For example, the score Z1 may be a value that corresponds to the alignment error (absolute value) with the minus sign, in other words, calculated through the following formula: Z1=−|D|.

The score Z2 is based on an amount of defects of the ring image received on the imaging element for measurement 54. The amount of defects corresponds to an error, from a theoretical value, of the number of spots consisting of the ring image detected on the imaging element for measurement 54. The score Z2 is defined to show a smaller value as the amount of defects increases and to show a greater value as the amount of defects decreases.

The score Z3 is based on an amount of deformation of the ring image detected on the imaging element for measurement 54. The amount of deformation corresponds to an error of the ring image from a theoretical shape. The score Z3 is defined to show a smaller value as the deformation increases in amount and to show a greater value as the deformation decreases in amount.

The score Z4 is based on a difference of the measured value from an average value or a median. The score Z4 is defined to show a smaller value as the difference increases and to show a greater value as the difference decreases. The score Z4 can be calculated after the specific number of measured values are obtained during the consecutive measurement of the refractive power.

Further, the control device 70 determines a display color of the measured value in accordance with the calculated reliability (S450). For example, the control device 70 determines at which of the following levels "high", "intermediate", or "low" the reliability of the measured value is placed in accordance with a specific determination criteria.

The control device 70 determines that the display color is a first color (for example, "red") when the reliability is at the "low" level. The control device 70 determines that the display color is a second color, which is different from the first color (for example, "white"), when the reliability is at the "intermediate" level. The control device 70 determines that the display color is a third color, which is different from the first color and the second color (for example, "blue"), when the reliability is at the "high" level.

Then, the control device 70 displays the latest measured value of the refractive power calculated in S430 on a real-time display area 751 of the display 75 in the display color determined in S450 (S460). As a result, the latest measured value is displayed on the display 75 together with its reliability as color information.

Figure 7:
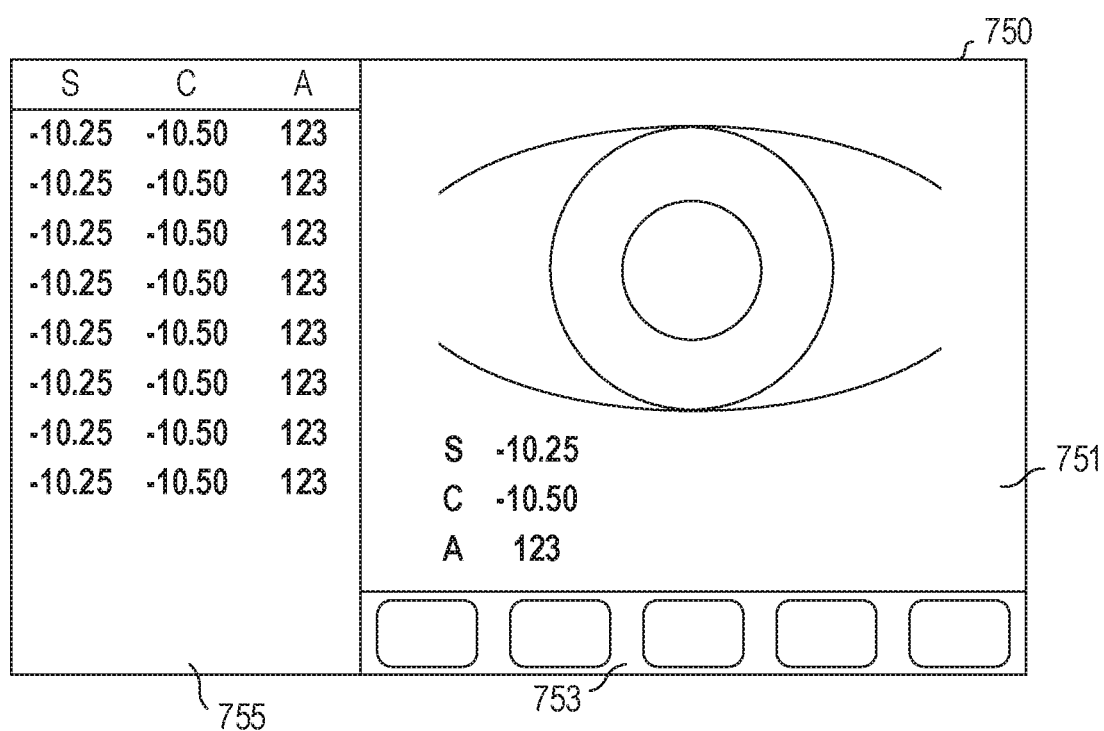
FIG. 7 is a view showing an example configuration of a screen displayed on a display.

In the second measurement process, the control device 70 can display a screen 750 shown in FIG. 7 on the display 75. The screen 750 includes the real-time display area 751, an operation object display area 753, and a list display area 755.

In accordance with the control device 70 controlling the display 75, the real-time display area 751 displays the latest measured value of the refractive power and the latest photographic image (real-time video image) of the anterior segment of the subject's eye E. If a previously measured value is displayed in the real-time display area 751, the control device 70 can control the display 75 so that the real-time display area 751 replaces the previously measured value with the latest measured value and displays the same (S460).

The operation object display area 753 displays the graphical user interface that includes operation objects. The list display area 755 displays a list of measured values obtained in the consecutive measurement. Specifically, the list display area 755 displays a list of measured values that have reliability equal to or greater than the standard reliability.

The control device 70 determines whether the latest measured value has the reliability equal to or greater than the standard reliability (S470). In response to determination that the reliability is equal to or greater than the standard reliability (S470: Yes), the control device 70 executes a list update process shown in FIG. 8 (S480). Consequently, the list display area 755 displays the list of the measured values having the reliability equal to or greater than the standard reliability. Here, the list of the measured values includes the latest measured value.

In response to determination that the reliability is below the standard reliability (S470: No), the control device 70 ends the repeated measurement process without additionally displaying the latest measured value in the list display area 755. In absence of the end command input by the examiner (S330: No), then the control device 70 executes the repeated measurement process again (S320).

Figure 8:
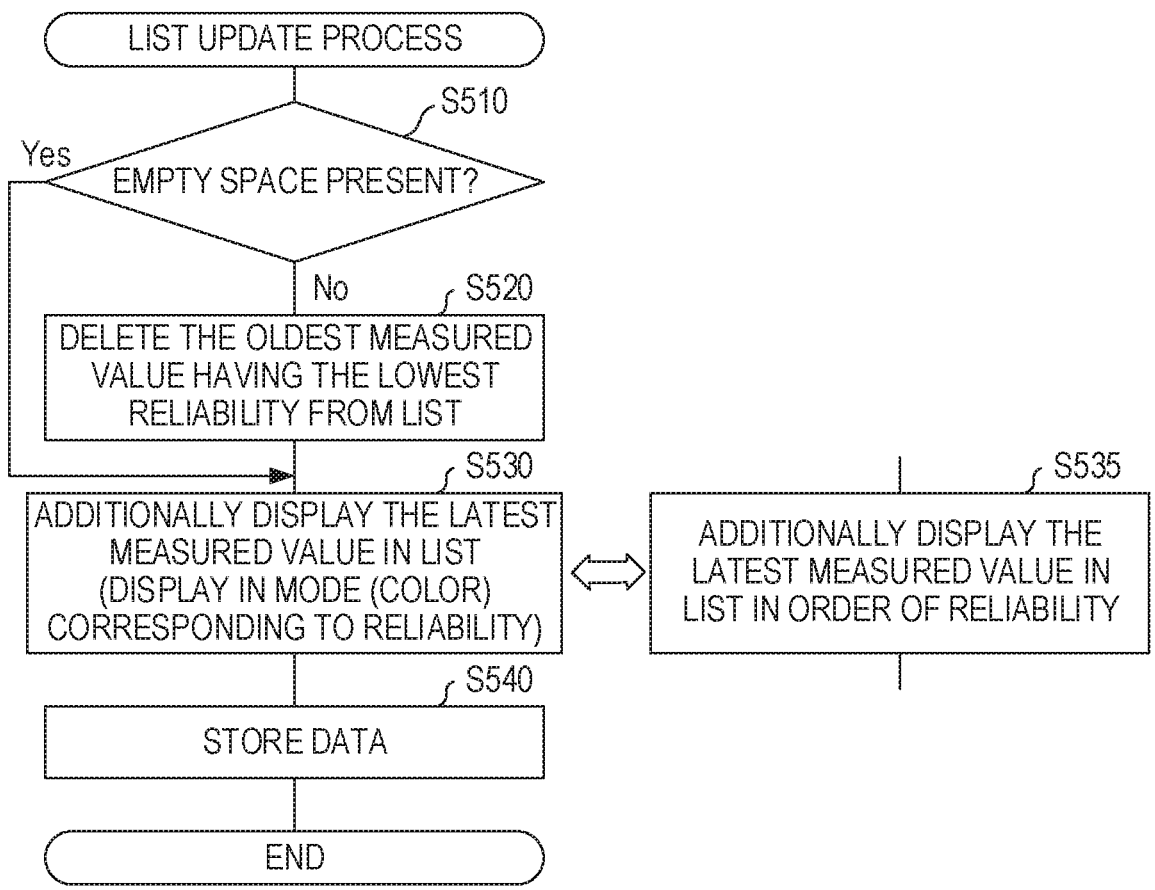
FIG. 8 is a flowchart showing a list update process executed by the control device.

A description is now given in detail to the list update process executed by the control device 70 in S480 with reference to FIG. 8. In response to a start of the list update process, the control device 70 determines whether the list display area 755 includes an empty space for additionally displaying the latest measured value (S510). In response to determination that the empty space is present (S510: Yes), the control device 70 executes a process in S530.

In response to determination that the empty space is not present (S510: No), the control device 70 deletes a measured value having the lowest reliability from the list display area 755 (S520). The measured value having the lowest reliability is one among a group of measured values displayed in the list display area 755, in other words, the list of the measured values. If the measured value having the lowest reliability consists of two or more measured values, then the control device 70 deletes a measured value having the lowest reliability and is the oldest measured value from the list display area 755 (S520). Then, the control device 70 executes the process in S530.

In S530, the control device 70 additionally displays the latest measured value in the list display area 755. The control device 70 can display the latest measured value in the color that is determined in S450 in accordance with the reliability. In one example, the measured values including the latest measured value are ordered chronologically to be listed and displayed in the list display area 755.

The control device 70 may execute a process in S535 in place of the process in S530. In S535, the control device 70 additionally displays the latest measured value in the list display area 755 such that the measured values including the latest measured value are ordered in an order of reliability to be listed and displayed.

Then, the control device 70 stores the latest measured value, which is additionally displayed in the list display area 755, in the memory 73 as the measurement history data (S540) and then ends the list update process (S480).

Figure 9:
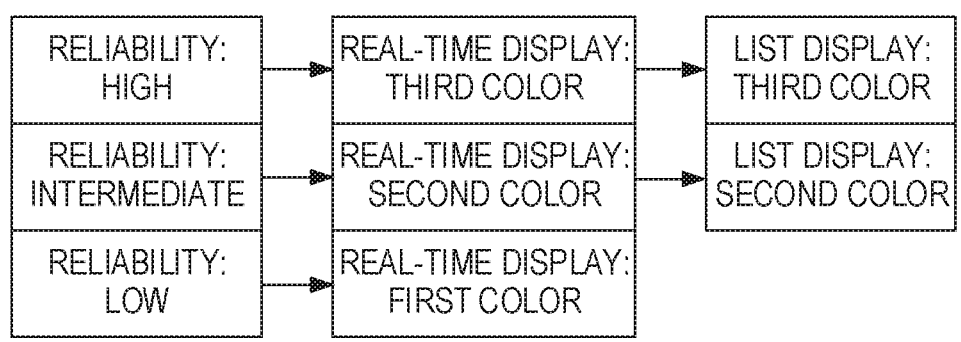
FIG. 9 is an explanatory diagram regarding displaying of a measured value in accordance with reliability.

According to the second measurement process, the refractive power of the subject's eye E is consecutively measured. In every end of each measurement, the latest measured value is displayed in the real-time display area 751 in the color corresponding to the reliability, as shown in FIG. 9. Consequently, the latest measured value and information on the reliability are displayed together in real-time on the display 75.

The latest measured value is additionally displayed in the list display area 755 if its reliability is equal to or greater than the standard reliability. This enables the latest measured value to be listed and displayed on the display 75 together with older measured values having the reliability equal to or greater than the standard reliability. According to an example shown in FIG. 9, the reliability equal to or greater than the standard reliability corresponds to the reliability equal to or greater than the "intermediate" level.

The measuring device 1 of the present embodiment described above is significant in that the consecutive measurement mode is included to measure the subject's eye E of a restless subject, particularly a child.

In measuring the eye refractive power, it is preferable to execute the automatic fogging to relax the subject's eye E. In the case of the restless subject, however, an alignment state between the subject's eye E and the device optical system 3 is unstable. Thus, it is difficult or it takes time to properly execute the automatic fogging. The automatic fogging has a poor effect on the restless subject in comparison with a sedate adult. Additionally, as the measurement takes prolonged time, a child becomes uncooperative.

In view of the aforementioned difficulty and time consuming nature of the automatic fogging executed on the restless subject, the consecutive measurement mode (the second measurement process) enables the consecutive measurement of the refractive power to be started promptly in response to the input of the start command from the examiner through the input interface 79 without executing the preliminary measurement and the automatic fogging and to be executed until the end command is input. This consecutive measurement increases the number of measurement per unit time, thus obtaining a greater amount of measured values having higher reliability within a short period of time in a proper alignment state.

According to the measuring device 1 of the present embodiment, it is also significant to sequentially display each measured value on the display 75 in every end of each measurement during the consecutive measurement. In this sequential display, the measured value is displayed on the display 75 in a display mode corresponding to its reliability, specifically, in the color corresponding to the reliability. This allows the information on the reliability to be displayed on the display 75 together with the measured value.

Accordingly, the examiner can properly grasp a situation on whether a proper measurement is executed based on information displayed on the display 75. This grasp enables the examiner to properly deal with the situation and to end a proper examination within a short period of time. Specifically, the examiner allows the measuring device 1 to continue the consecutive measurement until a required measurement result is obtained and can input the end command in response to obtainment of the required measurement result, to thereby promptly end the consecutive measurement.

In the present embodiment, the consecutive measurement without the automatic fogging enables the examiner to obtain a greater amount of measured values within a short period of time. In addition, real-time display of the measured value and the reliability enables the examiner to easily grasp whether the proper measurement is executed during the consecutive measurement. Thus, the measuring device 1 of the present embodiment is advantageously suitable for the restless subject.

In the present embodiment, in particular, the measured value having the higher reliability is displayed also in the list display area 755, enabling the examiner to deeply grasp a status of eye examination executed through the consecutive measurement.

Further, in the present embodiment, when the list of the measured values displayed on the screen 750 is full, a measured value having lower reliability and an older measured value are preferentially deleted from the list in order to leave valuable information on the list as much as possible for the examiner.

Therefore, in the present embodiment, examiner's desired measurement information of the refractive power is listed and displayed in an easily understandable manner. Particularly, it is possible to provide the examiner's desired information in a further understandable manner according to an example in which the measured values are listed and displayed in the list display area 755 in an order of the reliability (S535).

In one example, the reliability is determined based on the position of the subject's eye E and spatial distribution of the reflected light. Specifically, the reliability is determined based on the alignment error of the subject's eye E and, and the amount of defects of the ring image and the amount of deformation. According to this configuration, it is possible to more properly determine the reliability.

In the present embodiment, the consecutive measurement mode and the standard measurement mode are switched from each other for mode execution based on selection of the examiner. This mode switch enables the examiner to execute measurement of the refractive power that is adapted advantageously for adults and measurement of the refractive power that is adapted advantageously for children. According to the present embodiment, it is therefore possible to provide an eye refractive power measuring device having enhanced convenience.

It should be noted that the present disclosure is not limited to the above-described embodiment may be practiced in various modes. In the above-described embodiment, the consecutive measurement ends based on the end command from the examiner through the input interface 79. However, the control device 70 may operate such that the consecutive measurement ends based not on the end command. For example, the control device 70 may operate such that the consecutive measurement ends on a condition that the measured value having the reliability equal to or greater than the standard reliability is obtained a specific number of times after the consecutive measurement starts.

The list display area 755 may display a measured value having the reliability below the standard reliability. If the display 75 has a limited display area, it is also considered that the list display area 755 may not be included in the display 75.

In other words, the measuring device 1 may be configured such that the measured value is displayed in real-time, but is not displayed in a listing manner. In this case, the measuring device 1 can store the measured value of each measurement in the memory 73 and provide the examiner with the list of the measured values together with the information on the reliability in the form of a printed material, for example, after the eye examination ends. The list of the measured values may be provided as a digital data from the measuring device 1 to the external information processing device.

The measuring device 1 may be configured to display a first screen on the display 75 during the consecutive measurement and to display a second screen on the display 75 in response to an end of the consecutive measurement. The first screen consists of the above-described real-time display area 751, but not of the list display area 755. The second screen consists of the list display area 755 in place of the real-time display area 751. In other words, the measuring device 1 may be configured to display the list of the measured values on the display 75 only in response to the end of the consecutive measurement.

The process executed by the control device 70 may not follow the above-explained procedures. For example, the process includes steps in which even an altered execution order leads to the same result. In this case, an execution order of such steps is not limited to the above-described order. Some steps may be executed concurrently.

For example, the control device 70 may be configured to concurrently execute the following processes: capturing the light-receiving signal from the imaging element for measurement 54 to calculate the measured value of the refractive power; and calculating the alignment index value based on the respective detection signals from the alignment detection sensors 36 and 38. In this case, the alignment detection sensors 36 and 38 each can execute detection operation in a shorter cycle than a cycle in which the imaging element for measurement 54 executes imaging operation so that the control device 70 accurately calculates the alignment index value during the measurement.

The control device 70 may repeatedly calculate the alignment index value in a shorter cycle than a cycle in which the measured value of the refractive power is calculated. For example, the control device 70 may calculate the measured value of the refractive power in 200 milliseconds per cycle and may calculate the alignment index value in 20 milliseconds per cycle.

The measuring device 1 may be configured to be able to simultaneously measure respective refractive powers of both eyes of the aforementioned subject or to measure the respective refractive powers of both eyes in a switching manner in accordance with a command from the examiner. In order to achieve this, the measuring device 1 can individually comprise multiple configurations for the left and the right eyes, in which each configuration corresponds to at least a part of the device optical system 3 and a part of the control system 7. In this case, a measured value of each refractive power of each eye can be displayed on the display 75 in at least one of a real-time display mode or a listing display mode.

The measuring device 1 may be configured such that the measurement mode is automatically switched from the standard measurement mode to the consecutive measurement mode in response to satisfaction of a specific condition after the measuring device 1 starts operating in the standard mode.

Figure 10:
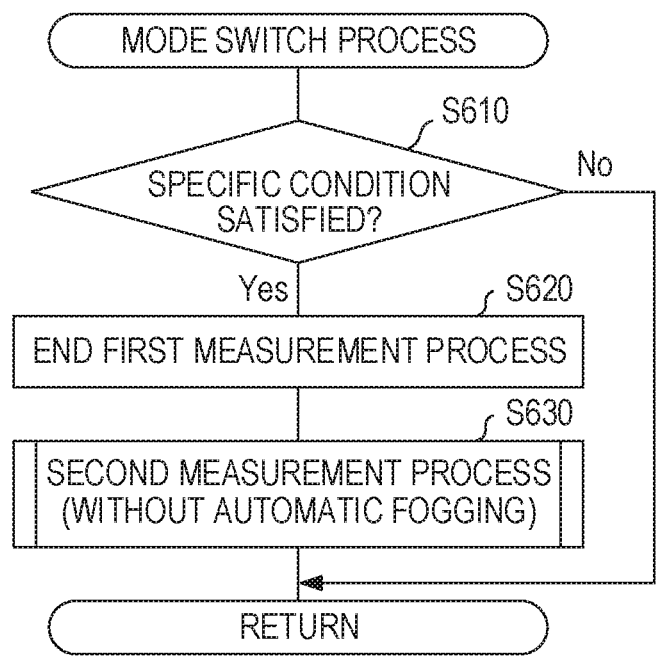
FIG. 10 is a flowchart showing a mode switch process executed by the control device.

For example, the control device 70 may be configured to repeatedly and concurrently execute a mode switch process shown in FIG. 10 during execution of the first measurement process (S130). In this example configuration, the control device 70 continues the first measurement process in response to determination that the specific condition is not satisfied (S610: No); and the control device 70 stops the first measurement process (S620) and starts the second measurement process (S630) in response to determination that the specific condition is satisfied (S610: Yes). The specific condition may be based on failure of the measurement and/or the reliability of the measured value.

For example, the measuring device 1 may be configured to automatically switch the measurement mode to the consecutive measurement mode when the measurement is failed multiple times consecutively in the standard measurement mode. The measuring device 1 may be configured to automatically switch the measurement mode to the consecutive measurement mode if what is obtained is only a measured value having the reliability below specific standard reliability (for example, the measured value having the reliability at "the lowest" level).

Alternatively, the measuring device 1 may be configured to display a message on the display 75 to thereby propose switching the measurement mode to the consecutive measurement mode. The message may say, "Switch to the consecutive measurement mode?", for example. The measuring device 1 can thereafter switch the measurement mode from the standard measurement mode to the consecutive measurement mode in accordance with the command from the examiner.

Moreover, a function of one element in the above-described embodiment may be divided and performed by two or more elements. A function of two or more elements may be integrated and performed by one element. A part of the configuration of the above-described embodiment may be omitted. It should be noted that any and all modes that are encompassed in the technical ideas defined by the languages in the claims are embodiments of the present disclosure.

Finally, explanations are given to correspondence between terms. The light-projecting optical system OS41 corresponds to one example of the light projector. The light-receiving optical system OS42 corresponds to one example of the light receiver. The alignment detection optical system OS3 corresponds to one example of the detector. The input interface 79 corresponds to one example of the inputter.

EXPLANATION OF REFERENCE NUMERALS

1 . . . measuring device, 3 . . . device optical system, 7 . . . control system, 11, 12 . . . illumination light source, 20 . . . imaging element for observation, 22 . . . target light source, 24 . . . target, 34 . . . alignment light source, 36, 38 . . . alignment detection sensor, 40 . . . measuring light source, 54 . . . imaging element for measurement, 61 . . . first drive device, 62 . . . second drive device, 63 . . . third drive device, 64 . . . fourth drive device, 70 . . . control device, 71 . . . processor, 73 . . . memory, 75 . . . display, 79 . . . input interface, 750 . . . screen, 751 . . . real-time display area, 755 . . . list display area, E . . . subject's eye, OS1 . . . observation optical system, OS2 . . . target optical system, OS3 . . . alignment detection optical system, OS4 . . . eye refractive power measuring optical system, OS41 . . . light-projecting optical system, OS42 . . . light-receiving optical system

What is claimed is:

1. An eye refractive power measuring device, comprising:
   a light projector configured to project a measuring light toward a fundus of a subject's eye;
   a light receiver configured to receive a reflected light that is reflected from the fundus;
   an inputter configured to input a command from an operator; and
   a controller,
   wherein the controller is configured to start a consecutive measurement process of an eye refractive power of the subject's eye without automatic fogging in response to input of a start command through the inputter, the consecutive measurement process including:
     consecutively executing a process that measures the eye refractive power of the subject's eye an undetermined number of times based on a light-receiving signal from the light receiver without automatic fogging until an end of the consecutive measurement process;
     determining reliability of a measured value of the eye refractive power in every execution of the process; and
     displaying, in every execution of the process, the measured value on a display together with information indicating the reliability,
   wherein the controller ends the consecutive measurement process in response to input of an end command through the inputter or in response to the measured value having the reliability equal to or greater than standard reliability being obtained a specific number of times.

2. The eye refractive power measuring device according to claim 1, wherein the controller displays the measured value on the display in a display mode that corresponds to the reliability among specific display modes, to thereby display the measured value on the display together with the information on the reliability.

3. The eye refractive power measuring device according to claim 2, wherein the controller displays the measured value on the display in a color that corresponds to the reliability among specific colors.

4. The eye refractive power measuring device according to claim 1, wherein the controller displays, in a list display area of the display, a list of measured values of the eye refractive power obtained through execution of the process multiple times.

5. The eye refractive power measuring device according to claim 4, wherein, in every execution of the process, the controller adds a measured value of the eye refractive power obtained through a corresponding process in the list display area.

6. The eye refractive power measuring device according to claim 5, wherein the controller deletes, from the list display area, a measured value that has the lowest reliability among the measured values of the eye refractive power already displayed in the list display area when the list display area lacks an area to display a newly measured value of the eye refractive power in the list display area.

7. The eye refractive power measuring device according to claim 6, wherein, when the measured value that has the lowest reliability includes several measured values of different measurement times, the controller deletes the oldest measured value among the several measured values from the list display area.

8. The eye refractive power measuring device according to claim 1, wherein, among measured values of the eye refractive power obtained through execution of the process multiple times, the controller displays the latest measured value in a temporal display area in the display, and displays a list of measured values having reliability equal to or greater than standard reliability in a list display area in the display.

9. The eye refractive power measuring device according to claim 4, wherein the controller arranges the measured values displayed in the list display area in an order that corresponds to individual reliability.

10. The eye refractive power measuring device according to claim 1, further comprising:
a detector configured to detect a position of the subject's eye,
wherein the controller determines the reliability based on the position of the subject's eye that is detected by the detector.

11. The eye refractive power measuring device according to claim 10, wherein the controller further determines the reliability based on spatial distribution of the reflected light that is indicated by the light-receiving signal.

12. The eye refractive power measuring device according to claim 1,
wherein the controller is configured to measure in response to input of the start command, the eye refractive power in one of operation modes,
wherein the operation modes include a first operation mode and a second operation mode, and
wherein the controller placed in the first operation mode executes automatic fogging and thereafter measures the eye refractive power based on the light-receiving signal from the light receiver, and the controller placed in the second operation mode starts the consecutive measurement process without executing the automatic fogging.

13. The eye refractive power measuring device according to claim 12, wherein, in response to a specific condition being satisfied after the controller starts operating in the first operation mode, the controller starts operating in the second operation mode in place of the first operation mode, to thereby start the consecutive measurement process without executing the automatic fogging.

14. The eye refractive power measuring device according to claim 13, wherein the controller starts operating in the second operation mode on a condition that measurement of the eye refractive power in the first operation mode is failed.

15. The eye refractive power measuring device according to claim 13, wherein the controller starts operating in the second operation mode on a condition that the reliability of a measured value of the eye refractive power in the first operation mode is below specific standard reliability.

16. A computer-implemented method of measuring an eye refractive power, the method comprising:
starting a consecutive measurement process of an eye refractive power of a subject's eye without automatic fogging in response to input of a start command through an inputter, the consecutive measurement process including:
consecutively executing a process an undetermined number of times without automatic fogging until an end of the consecutive measurement process, the process including:
projecting a measuring light toward a fundus of a subject's eye;
obtaining a light-receiving signal from an optical system that is configured to receive a reflected light reflected from the fundus; and
measuring an eye refractive power of the subject's eye based on the light-receiving signal;
determining reliability of a measured value of the eye refractive power in every execution of the process;
displaying, in every execution of the process, the measured value on a display together with information that indicates the reliability; and
ending the consecutive measurement process in response to input of an end command through the inputter or in response to the measured value having the reliability equal to or greater than standard reliability being obtained a specific number of times.

17. The method of measuring an eye refractive power according to claim 16, the method further comprising:
measuring the eye refractive power of the subject's eye in a specified operation mode of operation modes in response to input of a start command through the inputter;
executing, in a first operation mode of the operation modes, automatic fogging, thereafter obtaining a light-receiving signal from the optical system, measuring the eye refractive power of the subject's eye based on the light-receiving signal, and displaying the measured value of the eye refractive power on the display; and
starting, in a second operation mode of the operation modes, the consecutive measurement process without executing automatic fogging, and ending the consecutive measurement process in response to input of an end command through the inputter or in response to the measured value having the reliability equal to or greater than the standard reliability being obtained a specific number of times.

18. The eye refractive power measuring device according to claim 1, wherein the controller determines the reliability based on spatial distribution of the reflected light that is indicated by the light-receiving signal.

19. The eye refractive power measuring device according to claim 18, wherein the controller determines the reliability based on at least one of an amount of defects of a ring image or an amount of deformation of the ring image that is indicated by the light-receiving signal corresponding to spatial distribution of the reflected light.

20. The eye refractive power measuring device according to claim 8, wherein the controller displays the latest measured value in the temporal display area in the display in a display mode corresponding to the reliability of the latest measured value.

* * * * *